(12) United States Patent
Rigert et al.

(10) Patent No.: US 10,434,230 B2
(45) Date of Patent: Oct. 8, 2019

(54) ADAPTER WITH MEDIA SEPARATING DIAPHRAGM FOR A BREAST SHIELD

(71) Applicant: MEDELA HOLDING AG, Baar (CH)

(72) Inventors: Mario Rigert, Buchrain (CH); Bernhard Emmenegger, Lucerne (CH)

(73) Assignee: MEDELA HOLDING AG, Baar (CH)

(*) Notice: Subject to any disclaimer, the term of this patent is extended or adjusted under 35 U.S.C. 154(b) by 113 days.

(21) Appl. No.: 15/550,983

(22) PCT Filed: Feb. 9, 2016

(86) PCT No.: PCT/EP2016/052711
§ 371 (c)(1),
(2) Date: Aug. 14, 2017

(87) PCT Pub. No.: WO2016/131677
PCT Pub. Date: Aug. 25, 2016

(65) Prior Publication Data
US 2018/0021491 A1      Jan. 25, 2018

(30) Foreign Application Priority Data

Feb. 20, 2015    (EP) .................................... 15155892

(51) Int. Cl.
*A61M 1/06*          (2006.01)
*A61M 1/00*          (2006.01)

(52) U.S. Cl.
CPC .......... *A61M 1/062* (2014.02); *A61M 1/0049* (2013.01); *A61M 1/06* (2013.01)

(58) Field of Classification Search
CPC ....... A61M 1/0049; A61M 1/062; A61M 1/06
See application file for complete search history.

(56) References Cited

U.S. PATENT DOCUMENTS

| 5,941,847 A | 8/1999 | Huber et al. |
| 2004/0087898 A1 | 5/2004 | Weniger |

(Continued)

FOREIGN PATENT DOCUMENTS

| CN | 202184978 U | 4/2012 |
| CN | 202942469 U | 5/2013 |

(Continued)

OTHER PUBLICATIONS

International Search Report for Application No. PCT/EP2016/052711, dated May 2, 2017.

(Continued)

*Primary Examiner* — Bhisma Mehta
*Assistant Examiner* — Nidah M Hussain
(74) *Attorney, Agent, or Firm* — Marshall, Gerstein & Borun LLP

(57) ABSTRACT

An adapter for a breast shield of a breast pump for pumping human breast milk has a chamber having a first opening leading to the breast shield and a second opening remote from the breast shield. The adapter also has a flexible media separation diaphragm, which is accommodated in the chamber and separates the chamber into a pump-side and a breast-shield-side area. The chamber tapers toward the breast-shield-side opening. The chamber has the shape of a spherical dome which is cut off in the tapering area thereof. The media separation diaphragm likewise has substantially the shape of a flattened spherical dome having a flat top side, wherein the flat top side of the media separation diaphragm faces the breast-shield-side opening of the chamber. The adapter permits a minimum pressure drop over the media separation diaphragm and ensures a reliable return to the original shape of the media separation diaphragm.

15 Claims, 5 Drawing Sheets

(56) References Cited

U.S. PATENT DOCUMENTS

| | | | |
|---|---|---|---|
| 2008/0171970 A1* | 7/2008 | Luzbetak | A61M 1/0049 |
| | | | 604/74 |
| 2010/0324477 A1 | 12/2010 | Paterson et al. | |
| 2012/0071820 A1 | 3/2012 | Luzbetak et al. | |

FOREIGN PATENT DOCUMENTS

| | | |
|---|---|---|
| EP | 1818067 A1 | 8/2007 |
| WO | WO-01/47577 A2 | 7/2001 |
| WO | WO-2008/057218 A2 | 5/2008 |
| WO | WO-2011/035447 A1 | 3/2011 |
| WO | WO-2014/094187 A1 | 6/2014 |

OTHER PUBLICATIONS

Chinese First Office Action for Application No. 201680010845.6, dated Mar. 22, 2019.

* cited by examiner

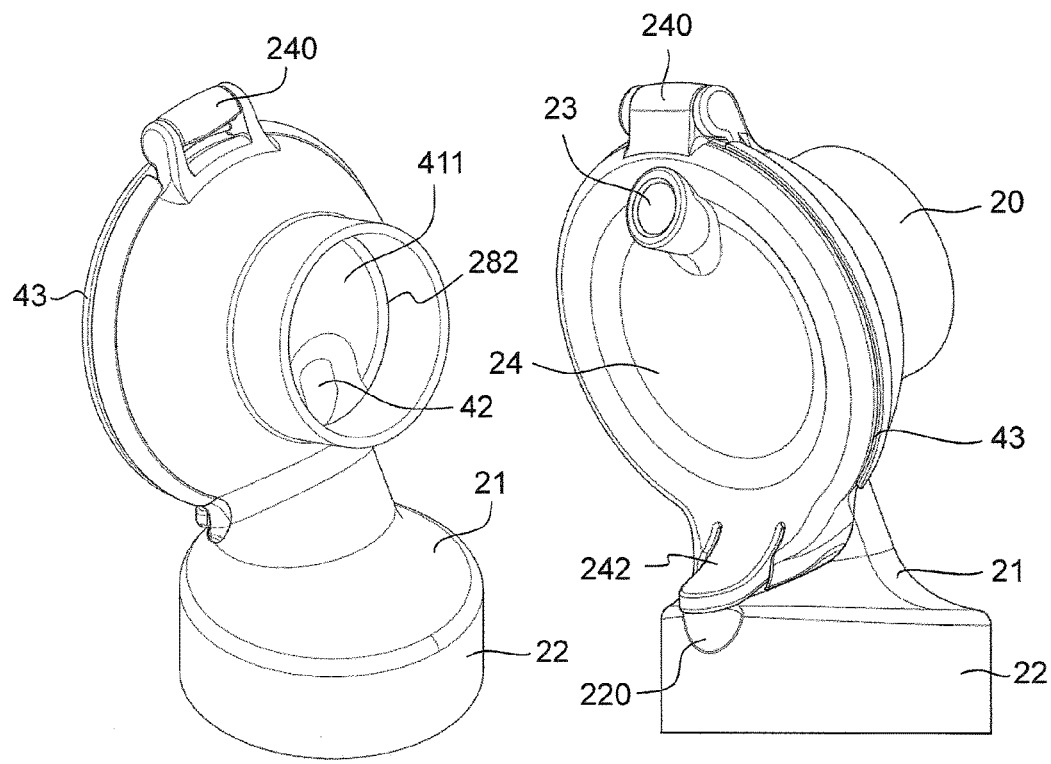
FIG. 6
FIG. 7
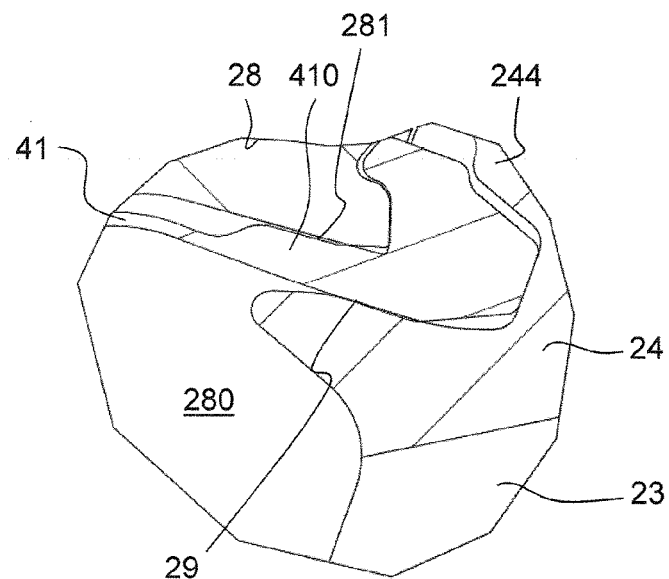
FIG. 5

ADAPTER WITH MEDIA SEPARATING DIAPHRAGM FOR A BREAST SHIELD

CROSS-REFERENCE TO RELATED APPLICATION

The present application is the US national phase of International Application No. PCT/EP2016/052711, filed Feb. 9, 2016, which claims priority to European Application No. 15155892.1, filed Feb. 20, 2015. The priority application EP 15155892.1, is hereby incorporated by reference.

TECHNICAL FIELD

The present invention relates to an adapter having a media separating diaphragm for a breast shield of a breast pump for expressing human breast milk.

PRIOR ART

Breast pump systems for expressing human breast milk are well known. They comprise a vacuum pump which is operated manually or by electric motor, at least one breast shield for placing on the breast and one milk collecting container in which the expressed milk is caught. The breast shield is connected to the vacuum pump directly or by means of a suction line such that a cyclically varying negative pressure can be applied to the breast in the breast shield in order to express the milk from the breast.

Known breast shields are held releasably in an adapter or are fixedly connected to the same. The adapter serves for the connection to a milk collecting container and to a vacuum pump. The pump, in this case, can be connected to the adapter by means of a suction line or can be arranged directly on said adapter. The milk collecting container, usually a bag or a bottle, is also fastened directly in a releasable manner on the adapter or is connected to said adapter by means of a milk line.

WO 01/47577 shows these types of breast shields. They are each connected to the vacuum pump by means of a suction hose, on the pump-side end of the suction hose there being a cap with a media separating diaphragm held thereon. Said cap, together with the media separating diaphragm, is pulled onto the pump diaphragm of the vacuum pump and together with the pump diaphragm forms the pump chamber. The media separating diaphragm fits snugly to the surface of the pump diaphragm and is moved in cyclical movements together with said pump diaphragm. Thanks to the media separating diaphragm, the pump region is protected from contaminants and contamination as it separates the medium "air in the vacuum pump" from the medium "air and milk in the breast shield". It protects in particular against expressed breast milk and bacteria passing into the suction hose. This same pump can be used by several mothers as a result. It can be used in an optimum manner in particular in hospitals and it can be hired out.

WO 2011/035447 shows a very simple, cylindrical adapter which is connected to just one line. Said line serves both as a suction line and as a milk line. The media separating diaphragm, which also conveys the milk into a milk collecting container, is arranged at the pump-side end of the suction line and in front of the vacuum pump. It transmits the cyclically generated negative pressure by means of the suction line to the breast shield and consequently to the breast.

In addition, breast pump systems are known where the media separating diaphragm is arranged at the breast-shield-side end of the suction hose in an adapter of the breast shield. Said media separating diaphragm also transmits the cyclically generated negative pressure from the vacuum pump into the breast shield and protects the suction hose and the vacuum pump from contaminants.

U.S. Pat. No. 5,941,847 discloses a foldable media separating diaphragm of this type which is realized in a cylindrical shape and is arranged in the cylindrical connecting pieces of the breast shield.

WO 2014/094187 describes a media separating diaphragm which is situated at least sometimes in the breast shield region into which the nipple projects.

The media separating diaphragm according to US 2010/0324477 is arranged in an upper region of the adapter and is covered by way of a rotary cover. The diaphragm is realized in a circular shape with ring-shaped elevations and indentations.

US 2004/0087898 shows a semi-spherical-shaped media separating diaphragm which is held in a sealing manner between two adapter parts. The adapter part remote from the breast shield comprises a container connection for fastening a milk collecting container. A non-return valve is arranged in said connection part. The media separating diaphragm can be mounted by the adapter part on the breast shield side being pivoted about an axis.

WO 2008/057218 proposes using a prestressed diaphragm instead of a foldable media separating diaphragm. The adapter is developed in a relatively complex manner.

Soft, collapsing media separating diaphragms require a resetting force provided by the vacuum pump in order to regain their original form. There is always the risk that they are no longer able to assume their original form fully in the course of the expressing operation and consequently can no longer transmit the cyclically applied negative pressure in an optimum manner.

The disadvantage of more rigid media separating diaphragms is that they comprise a larger pressure drop over the diaphragm. This is a problem in particular in the case of large size shields or funnels as in these cases the pump pick-up volume of the breast pump system is often no longer great enough in order to apply a sufficient negative pressure to the breast.

DISCLOSURE OF THE INVENTION

It is an object of the invention to create an adapter with a media separating diaphragm which enables as small a pressure drop as possible over the media separating diaphragm, it nevertheless being possible to reset the media separating diaphragm reliably into its original form.

In the adapter according to the invention for a breast shield of a breast pump for expressing human breast milk, the breast shield is connected so as to be holdable or is integrally connected in one piece to said adapter. The adapter comprises a suction connection for connection to a vacuum pump and a milk connection for connection to a milk collecting container. The adapter further comprises a chamber, from which the suction connection and a milk outlet opening lead, the chamber further comprising an opening on the breast shield side that leads to the breast shield with a first diameter and an opening remote from the breast shield with a second diameter. The adapter additionally comprises a flexible media separating diaphragm which is received in the chamber and separates the chamber into a pump-side region and a breast-shield-side region for the purposes of transmitting a negative pressure generated by the vacuum pump into the breast shield and for the purposes of protecting the vacuum pump against contamination. The chamber tapers toward the opening on the breast shield side and comprises the form of a spherical calotte which is cut off in its tapering region. The media separating diaphragm comprises substantially the form of a flattened spherical calotte with an even top surface and the even top surface of the media separating diaphragm faces the opening of the chamber on the breast shield side.

Said special form of the chamber in which the cyclical negative pressure generated by the vacuum pump is transmitted with the media separated, and the form of the media separating diaphragm matched thereto make it possible for a very thin, preferably limp media separating diaphragm to be used. The pressure drop over the diaphragm is minimized as a result. It is usually between 1 and a maximum of 10 mmHg.

A further advantage is that the adapter is able to be realized as simply as possible, with a minimum of parts and consequently in a cost-efficient manner. The assembling of the adapter is easy to understand for the mother and hardly requires any time. In particular, the media separating diaphragm can be changed, cleaned and re-installed again in the chamber in a simple manner. The entire adapter can be cleaned in an optimum manner as it consists predominantly of large surfaces without interruptions and above all comprises large easily accessible openings and simply developed sealing edges and surfaces.

The method of operation of the media separating diaphragm is optimized when the even top surface of the media separating diaphragm comprises a diameter which corresponds approximately to the diameter of the opening on the breast shield side.

The chamber preferably tapers steplessly toward the opening in the region of the opening on the breast shield side. This optimizes the method of operation and facilitates cleaning.

The media separating diaphragm preferably abuts substantially against an inside surface of the chamber in the non-loaded state without negative pressurization. In said preferred embodiment, the media separating diaphragm is consequently in particular not prestressed and the chamber consequently forms substantially the counterpart to the media separating diaphragm.

The media separating diaphragm is preferably limp. It needs a resetting force in order to regain its original shape quickly enough during the pumping cycle, i.e. in this case its spherical segment-shaped shape. Said resetting force is ensured by means of the vacuum pump by the vacuum being released.

In a preferred embodiment, the media separating diaphragm comprises an indentation which forms part of a milk channel between the opening on the breast shield side and the milk connection. Thanks to said indentation, the media separating diaphragm, abutting against the inside surface of the chamber, can extend approximately up to or completely up to the opening on the breast shield side and nevertheless the milk is able to flow unobstructed via the chamber toward the milk connection. The dead volume in the adapter is minimized as a result.

Said indentation is preferably situated in a transition region between the even top surface and a curved lateral surface of the flattened spherical calotte of the media separating diaphragm.

In a preferred embodiment, the chamber, in its spherical segment-shaped region, comprises a milk outlet opening. The media separating diaphragm preferably comprises a flexible valve flap which closes said milk outlet opening.

The integral realization of the media separating diaphragm with the valve flap simplifies the design of the adapter additionally. A separate part for the milk valve is not necessary. It can be mounted together with the rest of the media separating diaphragm, which facilitates assembly. In addition, there is no separate valve part which could be forgotten by the mother during assembly, which could be mistakenly flushed down the kitchen sink pipes during cleaning or which could be swallowed by a small child. In addition, the valve flap provides the precise position in which the media separating diaphragm is to be inserted into the chamber. This also facilitates assembly.

In a preferred embodiment, the media separating diaphragm comprises a circular circumferential edge which is realized in a thicker manner than the flattened spherical calotte and which is provided at least in portions with a positioning ring. The seal is simply designed, but extremely efficient. It can be obtained by a simple friction-locking fit. In addition, the thickened edge of the media separating diaphragm provides stability such that is sits well in the hand during assembly.

The adapter preferably comprises a basic body on the breast shield side and a cover remote from the breast shield, the chamber being arranged in the basic body and the cover closing the opening of the chamber remote from the breast shield. As a result, the chamber is accessible in a simple manner and the media separating diaphragm can be easily inserted and removed again.

In a preferred embodiment, the basic body comprises a circular circumferential first sealing edge, over which the media separating diaphragm can be pulled, the at least partially circumferential positioning ring surrounding said first sealing edge. The positioning ring is preferably not realized in a totally circumferential manner, a region for a pivoting hinge and/or for a snap-type closure of the adapter being left free.

As an alternative to this or in addition to it, the cover comprises a circular circumferential second sealing edge, over which the media separating diaphragm can be pulled by way of its circumferential edge, the circumferential edge abutting against the second sealing edge in a sealing manner.

The media separating diaphragm is preferably fastenable selectively on the cover or on the basic body, the sealing effect, when the cover is closed, being achieved on both sides of the media separating diaphragm by means of a frictional-locking fit. The adapter is reliably tight as a result.

When the cover is closed, the positioning ring of the media separating diaphragm preferably forms an outside surface of the adapter between the cover and the basic body. The ring is consequently visible from the outside with the cover closed. In addition, without the media separating diaphragm the adapter is not tight in order to express milk. As a result, the adapter is prevented twice over from being used without the media separating diaphragm and the vacuum pump from being exposed to contaminants or contamination.

The assembling of the adapter is facilitated when the cover is arranged on the basic body so as to be pivotable about one single pivot axis.

The media separating diaphragm of the above-described adapter comprises substantially the form of a flattened spherical calotte with an even top surface and, in preferred embodiments, has the features described above and below.

BRIEF DESCRIPTION OF THE DRAWINGS

A preferred embodiment of the invention is described below by way of the drawings which serve purely for explanation and are not to be deemed restrictive, in which:

FIG. 5 shows an enlarged representation of the region a according to FIG. 4;

FIG. 6 shows a perspective representation of the adapter according to FIG. 1 seen from the side of the breast shield;

FIG. 7 shows a perspective representation of the adapter according to FIG. 1 seen from the side remote from the breast shield;

DESCRIPTION OF PREFERRED EXEMPLARY EMBODIMENTS

Figure 13:
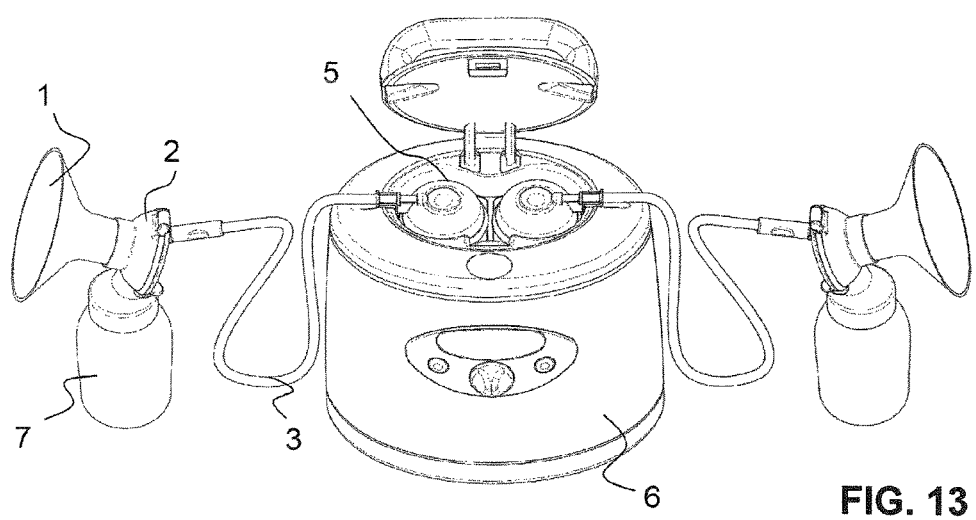
FIG. 13 shows a perspective representation of a breast pump system, a vacuum pump and with the adapter according to the invention.

FIG. 13 shows a breast pump system with a vacuum pump 6, a cap 5 placed onto a pump diaphragm of the vacuum pump 6, a suction line 3 which connects the cap 5 to the adapter 2, a breast shield 1 which is connected to the adapter 2 and a milk collecting container 7 which is also connected to the adapter 2. The breast shield 1 is preferably inserted into the adapter 2 and is connected releasably to it. However, it can also be integrally moulded in one piece on the adapter 2. A dual pump with two caps, two suction lines and two breast shield units is shown in this example.

The cap 5, adapter 2 and breast shield 1 preferably consist of plastics material, it preferably being possible for the cap 5 and the adapter 3 to be realized in a rigid manner and for the breast shield 1 to be realized in a rigid, soft or semi-soft manner.

The breast shield 1 shown here provides an independent invention. It is described in detail in the patent application by the same applicant that was filed on the same day with the title "Breast shield". The content of said patent application is hereby incorporated into this text by reference.

The cap 5 shown here also provides an independent invention. It is described in detail in the patent application by the same applicant that was filed on the same day with the title "Cap for a breast pump". The content of said patent application is hereby incorporated into this text by reference.

Figure 1:
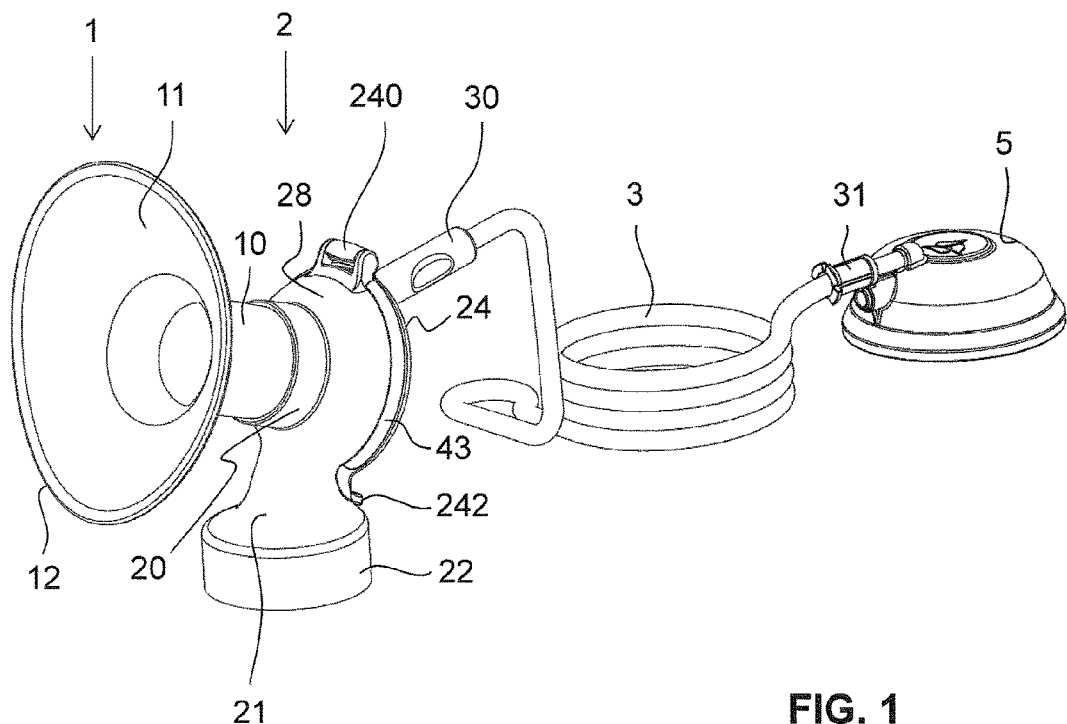
FIG. 1 shows a perspective representation of a breast pump system without a vacuum pump with the adapter according to the invention.
Figure 2:
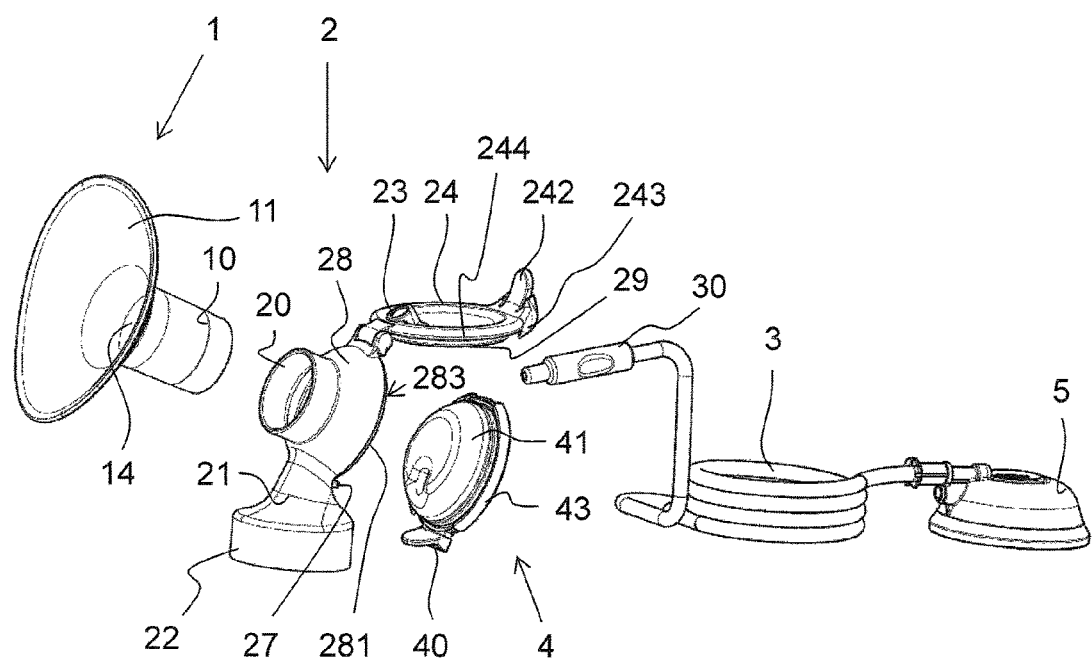
FIG. 2 shows an exploded drawing of the breast pump system according to FIG. 1.

FIGS. 1 and 2 show the breast pump system without a vacuum pump. The suction line 3 is preferably a flexible suction hose which is fixedly connected to the cap 5 by means of a pump-side connection plug 31 that cannot be removed without causing damage. On the other end, the suction line 3 comprises an adapter-side plug 30 which is preferably connectable in a releasable manner to a suction connection 23 of the adapter 2. It can be plugged-in here.

The breast shield 1 comprises a tubular connection part 10 and a funnel 11, which is integrally moulded thereon in one piece, for receiving a human breast and a supporting edge 12 for supporting the human breast. Haptic elements 13, here in the form of annular elevations, are present on the outside top surface of the funnel 11. A different breast shield of a known type can also be used in place of said breast shield 1.

Figure 3:
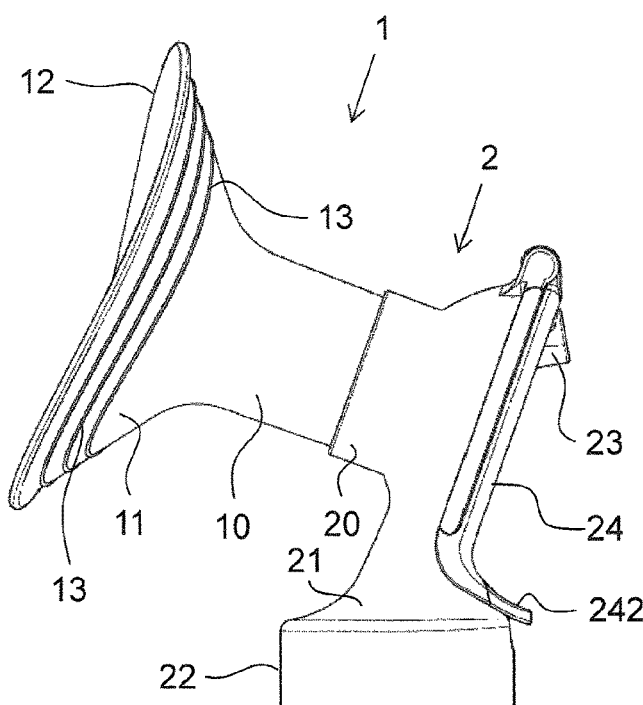
FIG. 3 shows a side view of the adapter according to FIG. 1 with a breast shield mounted.
Figure 4:
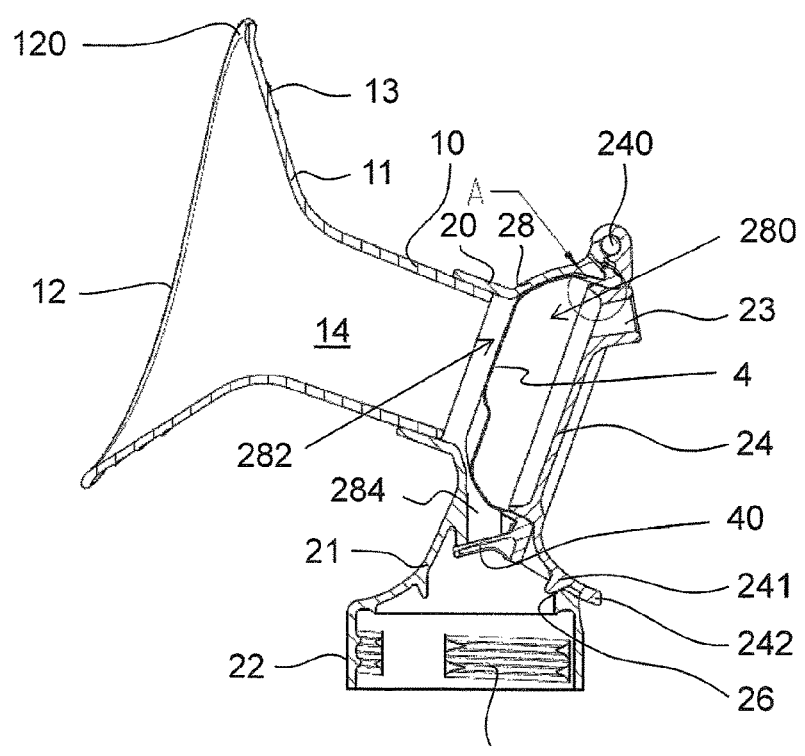
FIG. 4 shows a longitudinal section through the adapter according to FIG. 1 with the breast plate mounted.

As can easily be seen in FIGS. 2 to 4 as well as 6 and 7, the adapter 2 comprises a basic body 28 which is realized in a hollow manner and forms a chamber 280. A tubular receiving part 20, into which the connection part 10 of the breast shield 1 can be inserted, is integrally moulded on the basic body 28. The basic body 28 merges via a neck 21 into a tubular milk connection 22. Said milk connection is preferably provided with an internal thread 25. It serves for connection to a milk collecting container, in particular a milk bottle.

The breast shield 1 and the adapter 2 form a passage or milk channel 14 which extends from the end of the breast shield 1 close to the breast to the milk connection 22 and consequently enables milk to flow from the mother's breast into the milk collecting container.

The adapter 2 comprises a flexible media separating diaphragm 4 which is arranged in the chamber 280 of the basic body 28. To this end, the adapter 2 comprises a cover 24 so that the media separating diaphragm 4 is able to be inserted into the housing or into the basic body 28 of the adapter 2 and for the purposes of replacement or cleaning is also able to be removed therefrom. The cover 24, in this example, is connected to the basic body 28 by means of one single pivoting hinge 240. The pivoting hinge 240 is preferably arranged at the top. A handle 242, on the back of which a retaining lug 241 is realized, is integrally moulded on the oppositely situated bottom end. Said retaining lug 241 engages in a retaining edge 26 of an opening in the neck 21 of the adapter 2. As a result, a snap-type closure is formed. There is additionally a dent 220, which facilitates the gripping of the handle 242, on the milk connection 22.

A downwardly directed, curved flank 243 is integrally moulded as a positive locking closure on each of the two sides of the handle 242. The flanks 243 and the retaining edge 26 are preferably realized extending in an oblique manner.

The cover 24 is preferably realized in an approximately flat and substantially round manner. The suction connection 23 is integrally moulded in the top region of the cover 24.

The chamber 280 is realized in a spherical segment-shaped form, its tapering end being cut off and forming a first round opening 282 on the side of the breast shield. The diameter of said opening 282 on the side of the breast shield corresponds to the diameter of the tubular receiving part 20 and is consequently relatively large.

The end of the spherical segment-shaped chamber 280 remote from the breast shield forms a second round opening 283 remote from the breast shield. Said opening 283 remote from the breast shield is covered and closed by the cover 24. The chamber 280 can extend in a spherical segment-shaped form up to said opening 283 remote from the breast shield or, as in this example, it can have already merged beforehand into an approximately circular-cylindrical form.

As shown in FIG. 4, there is a milk outlet opening 284, through which expressed milk is able to flow into the milk collecting container, in the bottom region of the chamber 280. Said milk outlet opening 284 comprises a circumferential edge which is directed toward the milk connection 22 and forms a valve seat. A valve flap 40, which together with the valve seat forms a non-return valve and consequently delimits the dead volume in the adapter 2, is integrally moulded in one piece on the media separating diaphragm 4. The valve flap 40 protrudes at an angle, preferably of about 55°, from a circular circumferential edge 45 of the remaining diaphragm 4, as can easily be seen in FIG. 11. The valve flap 40 comprises, as can also be seen in FIG. 11, a web 400 which is applied to two lugs 249 of the cover 24. Said lugs can be seen in FIG. 12. A collar 401, which runs around the valve flap 40 and is directed downward, gives it stability.

The media separating diaphragm 4 comprises a basic body 41 which is also realized in the form of a flattened spherical calotte and on which the valve flap 40 is integrally moulded. Said basic body preferably does not comprise any irregularities at all, except for an indentation 42 that is mentioned below.

The flattened, round and even surface of the basic body 41 is provided with the reference 411 and is easy to see, for example, in FIGS. 8 to 11.

Said basic body 41 forms the counterpart to the chamber 280. In the mounted state, the basic body 41 abuts approximately or fully against the inside surface of the chamber 280, as can be seen in FIG. 4. The even surface 411, in this case, lies in the region of the opening 282 on the breast shield side or in said opening. Said surface 411 preferably comprises approximately or precisely the same diameter as said opening 282 on the breast shield side.

The mentioned indentation 42, which is shown as an elevation remote from the breast shield, is present in the transition region between the even surface 411 and the spherical segment-shaped region of the basic body 41. Said indentation 42 is arranged in the bottom region when the media separating diaphragm 4 is mounted in the correct manner and forms part of the milk channel 14 between the breast shield 1 and the milk connection 22. There can be a corresponding indentation situated opposite in the basic body 28 or in the neck 21 but this is not compulsory. None is present in this example.

The media separating diaphragm 4 is preferably produced from silicone. The basic body 41 is relatively thin, preferably limp. Typical thicknesses are between 0.2 and 1.0 mm. The valve flap 40 is preferably realized in a thicker manner.

Figure 10:
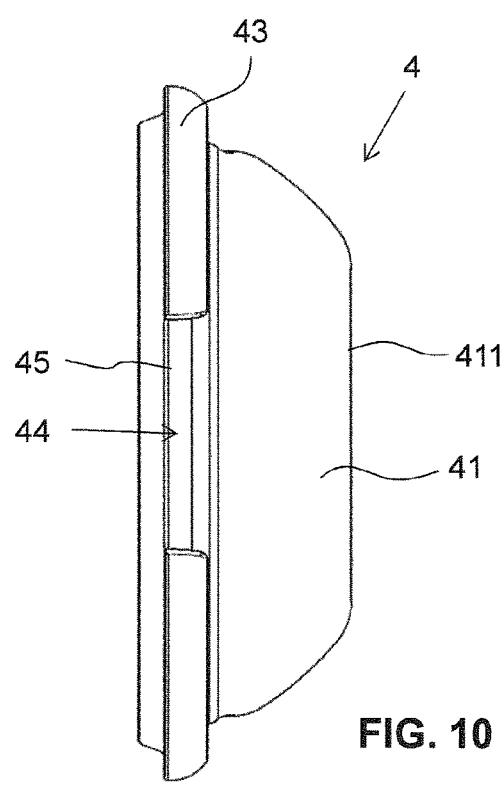
FIG. 10 shows a side view of the media separating diaphragm according to FIG. 8.
Figure 11:
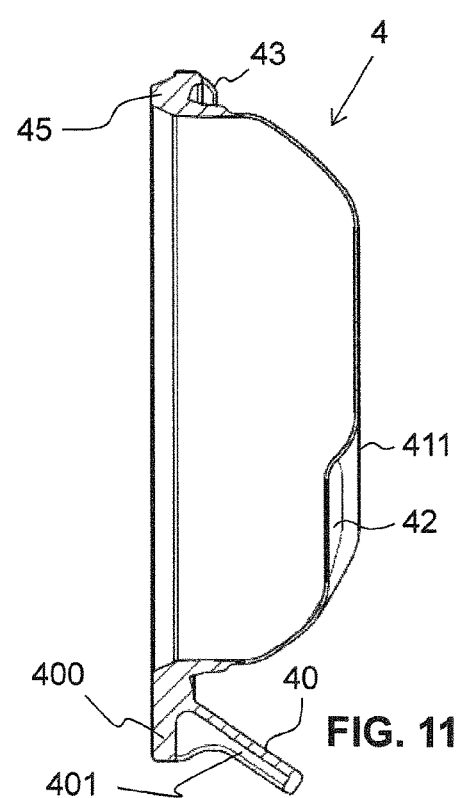
FIG. 11 shows a longitudinal section through the media separating diaphragm according to FIG. 8.
Figure 12:
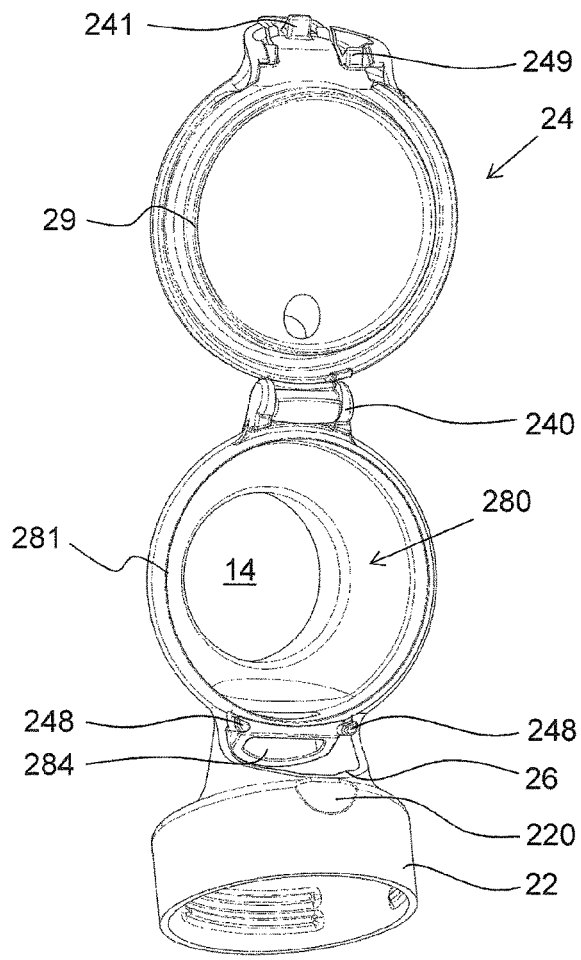
FIG. 12 shows a perspective view of the open adapter.

The basic body 41 is realized as a counterpart to the chamber 280. If the chamber 280 comprises a cylindrical portion remote from the breast shield, this also applies preferably to the basic body 41. This is the case here, as can be seen in FIGS. 10 and 11.

Remote from the breast shield, the basic body 41 comprises the circumferential, closed per se and circular circumferential edge 45 which is realized in a thickened manner and gives the basic body 41 its position and stability.

A thickening is provided with the reference numeral 410 in FIG. 5. Said thickening 410 seals in relation to a first sealing edge 281 of the basic body and in relation to a second sealing edge 29 of the cover. The sealing edges 281, 29 are realized in a circular circumferential manner and are closed per se and they preferably extend in a conical manner with respect to one another.

Figure 8:
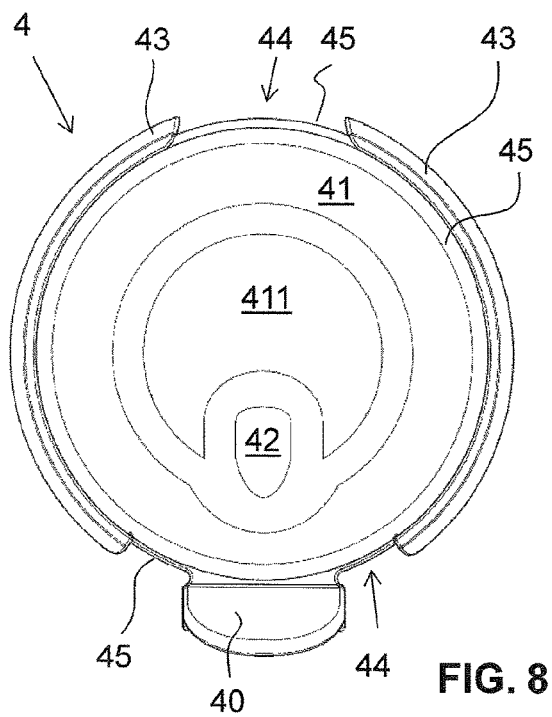
FIG. 8 shows a view from the side remote from the breast shield of a media separating diaphragm according to the invention of the adapter according to FIG. 1.
Figure 9:
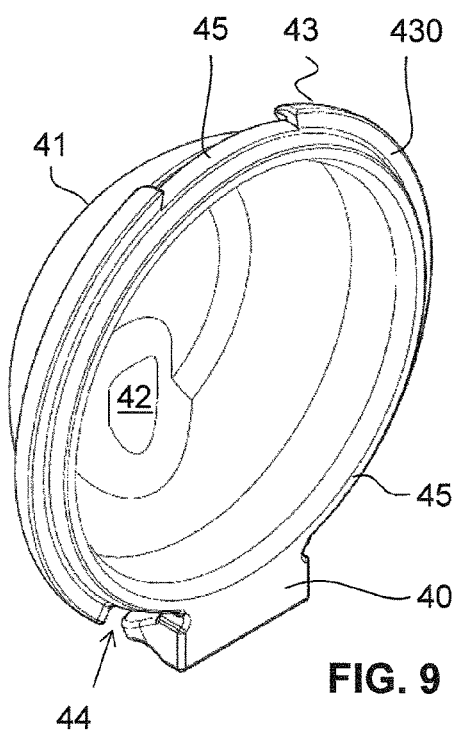
FIG. 9 shows a view from the side of the breast shield of the media separating diaphragm according to FIG. 8.

A positioning ring 43, which is also directed toward the breast shield, is additionally integrally moulded on the circumferential edge 45. Said positioning ring 43 is not realized in a totally circumferential manner, but rather there are recesses 44 in the region of the hinge 240 and of the handle 242, as can be seen in FIGS. 8 to 10.

It can be seen in FIG. 5 how the sealing is effected between the cover 24, the basic body 28 of the adapter 2 and the media separating diaphragm 4 in the region of the circumferential edge 45. The basic body 28 comprises the first sealing edge 281 which has already been mentioned, the outside diameter of which is smaller than the outermost diameter of the basic body 28 of the adapter. The first sealing edge 281 is formed by the edge of the opening 283 remote from the breast shield.

As can be seen in FIG. 1, with the cover 24 closed, the positioning ring 43 is clamped between the two parts of the adapter 2 and forms part of the outside surface of the adapter 2. The media separating diaphragm 4 is consequently visible from the outside. In addition, on account of the realization of the sealing surfaces, sealing edges and sealing lip, the adapter 2 is not tight when the media separating diaphragm 4 is not mounted. In addition, the hinged cover 24 cannot be closed when the media separating diaphragm 4 is not arranged in the correct position of rotation and situation. The media separating diaphragm 4 can, however, be mounted on either the cover 24 or on the basic body 28. If it is mounted on the cover 24, it is pulled over the second sealing edge 29, the valve flap 40 being placed or clamped between the two lugs of the cover. If it is mounted on the basic body 28, it is pulled over the first sealing edge 281, the valve flap 40 being placed or clamped between the two pins 27.

The adapter according to the invention enables a minimum pressure drop over the media separating diaphragm and ensures reliable resetting into its original form.

What is claimed is:

1. An adapter for a breast shield of a breast pump for expressing human breast milk, wherein the breast shield is one of holdable in the adapter or integrally connected in one piece to said adapter;
   wherein the adapter comprises a suction connection for connection to a vacuum pump and a milk connection for connection to a milk collecting container;
   wherein the adapter comprises a chamber from which the suction connection and a milk outlet opening lead;
   wherein the chamber additionally comprises an opening on a breast shield side which leads to the breast shield having a first diameter and an opening which is remote from the breast shield having a second diameter;
   and wherein the adapter additionally comprises a flexible media separating diaphragm which is received in the chamber and separates the chamber into a pump-side region and a breast-shield-side region for the purposes of transmitting a negative pressure generated by the vacuum pump into the breast shield and for the purposes of protecting against contamination of the vacuum pump;
   wherein the chamber tapers toward the opening on the breast shield side;
   wherein the chamber comprises the form of a spherical calotte which has been cut off in the chamber's tapering region;
   wherein the media separating diaphragm comprises substantially the form of a flattened spherical calotte with an even top surface;
   wherein the even top surface of the media separating diaphragm faces the opening of the chamber on the breast shield side; and
   wherein the media separating diaphragm comprises an indentation which forms part of a milk channel between the opening on the breast shield side and the milk connection.

2. The adapter according to claim 1, wherein the even top surface of the media separating diaphragm comprises a diameter which corresponds approximately to a diameter of the opening on the breast shield side.

3. The adapter according to claim 1, wherein the chamber tapers steplessly toward the opening on the breast shield side.

4. The adapter according to claim 1, wherein the media separating diaphragm abuts substantially against an inside surface of the chamber in a non-loaded state without negative pressurization.

5. The adapter according to claim 1, wherein the media separating diaphragm is limp.

6. The adapter according to claim 1, wherein the indentation is situated in a transition region between the even top surface and a curved lateral surface of the flattened spherical calotte of the media separating diaphragm.

7. The adapter according to claim 1, wherein the milk outlet opening is arranged in a spherical segment-shaped region of the chamber.

8. The adapter according to claim 7 wherein the media separating diaphragm comprises a flexible valve flap which closes said milk outlet opening.

9. The adapter according to claim 1, wherein the media separating diaphragm comprises a circular circumferential edge which is realized in a thicker manner than the flattened spherical calotte of the media separating diaphragm and which is provided at least in portions with a positioning ring.

10. The adapter according to claim 9, wherein a cover comprises a circular circumferential second sealing edge, over which the media separating diaphragm can be pulled by way of the circular circumferential edge of the media separating diaphragm, wherein the circular circumferential edge of the media separating diaphragm abuts in a sealing manner against the circular circumferential second sealing edge of the cover.

11. The adapter according to claim 9, wherein the adapter comprises a basic body on the breast shield side and a cover remote from the breast shield, wherein the chamber is arranged in the basic body and wherein the cover closes the opening of the chamber remote from the breast shield and wherein the basic body comprises a circular circumferential first sealing edge, over which the media separating diaphragm can be pulled, wherein the positioning ring, which is an at least partially circumferential positioning ring, surrounds said circular circumferential first sealing edge.

12. The adapter according to claim 11, wherein the cover comprises a circular circumferential second sealing edge, over which the media separating diaphragm can be pulled by way of the circular circumferential edge of the media separating diaphragm, wherein the circular circumferential edge of the media separating diaphragm abuts in a sealing manner against the circular circumferential second sealing edge of the cover and wherein, with the cover closed, the positioning ring of the media separating diaphragm forms an outside surface of the adapter between the cover and the basic body.

13. The adapter according to claim 1, wherein the adapter comprises a basic body on the breast shield side and a cover remote from the breast shield, wherein the chamber is arranged in the basic body and wherein the cover closes the opening of the chamber remote from the breast shield.

14. The adapter according to claim 1, wherein the cover is arranged on a basic body so as to be pivotable about one single pivot axis.

15. An adapter for a breast shield of a breast pump for expressing human breast milk, wherein the breast shield is one of holdable in the adapter or integrally connected in one piece to said adapter;
wherein the adapter comprises a suction connection for connection to a vacuum pump and a milk connection for connection to a milk collecting container;
wherein the adapter comprises a chamber from which the suction connection and a milk outlet opening lead;
wherein the chamber additionally comprises an opening on a breast shield side which leads to the breast shield having a first diameter and an opening which is remote from the breast shield having a second diameter;
and wherein the adapter additionally comprises a flexible media separating diaphragm which is received in the chamber and separates the chamber into a pump-side region and a breast-shield-side region for the purposes of transmitting a negative pressure generated by the vacuum pump into the breast shield and for the purposes of protecting against contamination of the vacuum pump;
wherein the chamber tapers toward the opening on the breast shield side;
wherein the chamber comprises the form of a spherical calotte which has been cut off in the chamber's tapering region;
wherein the media separating diaphragm comprises substantially the form of a flattened spherical calotte with an even top surface;
wherein the even top surface of the media separating diaphragm faces the opening of the chamber on the breast shield side; and
wherein a cover is arranged on a basic body so as to be pivotable about one single pivot axis.

* * * * *